(12) United States Patent
Hirama et al.

(10) Patent No.: US 7,399,470 B2
(45) Date of Patent: Jul. 15, 2008

(54) SANDWICH IMMUNOASSAY KITS FOR DETECTING CIGUATOXIN CTX3C

(75) Inventors: Masahiro Hirama, Sendai (JP); Hiroki Oguri, Sendai (JP); Ikuo Fujii, Sendai (JP); Takeshi Tsuburaya, Suita (JP)

(73) Assignee: Japan Science and Technology Agency, Saitama-ken (JP)

( * ) Notice: Subject to any disclaimer, the term of this patent is extended or adjusted under 35 U.S.C. 154(b) by 578 days.

(21) Appl. No.: 10/506,013

(22) PCT Filed: Mar. 10, 2003

(86) PCT No.: PCT/JP03/02782

§ 371 (c)(1),
(2), (4) Date: Aug. 30, 2004

(87) PCT Pub. No.: WO03/076934

PCT Pub. Date: Sep. 18, 2003

(65) Prior Publication Data

US 2005/0148041 A1  Jul. 7, 2005

(30) Foreign Application Priority Data

Mar. 12, 2002 (JP) ............... 2002-066754
Mar. 12, 2002 (JP) ............... 2002-066755

(51) Int. Cl.
*A61K 39/395* (2006.01)
*A61K 39/40* (2006.01)
*A61K 39/00* (2006.01)
*A61K 39/02* (2006.01)
*A61K 39/38* (2006.01)

(52) U.S. Cl. .............. 424/141.1; 424/130.1; 424/137.1; 424/156.1; 424/178.1; 424/236.1; 436/85; 436/91; 436/513; 436/543; 436/548; 530/387.1; 530/388.1; 530/388.2; 530/389.8; 435/283.1; 435/320.1; 435/325; 435/326; 435/332

(58) Field of Classification Search .............. 435/283.1, 435/320.1, 325, 326, 332, 345; 436/91, 513, 436/543, 547, 548; 530/387.1, 388.1, 388.9
See application file for complete search history.

(56) References Cited

U.S. PATENT DOCUMENTS

2004/0059096 A1  3/2004  Hirama et al.

FOREIGN PATENT DOCUMENTS

JP    08-201392    8/1996
WO   WO 03/016353 A1   2/2003

OTHER PUBLICATIONS

Hirama et al. 2001. Science. vol. 294: 1904-1907.*

(Continued)

*Primary Examiner*—Mark Navarro
*Assistant Examiner*—JaNa Hines
(74) *Attorney, Agent, or Firm*—Hahn & Voight; Roger C. Hahn

(57) ABSTRACT

A sandwich immunoassay kit for detecting ciguatoxins based on a combination of two anti-ciguatoxin CTX3C monoclonal antibodies produced by hybridomas, 3D11 (deposited at IPOD, AIST under accession number FMRM PB-8293) and 10C9 (FMRM PB-8292). In particular, one of the antibodies is labeled and each of them binds specifically to a different site of ciguatoxin CTX3C.

6 Claims, 3 Drawing Sheets

OTHER PUBLICATIONS

Figure 1:
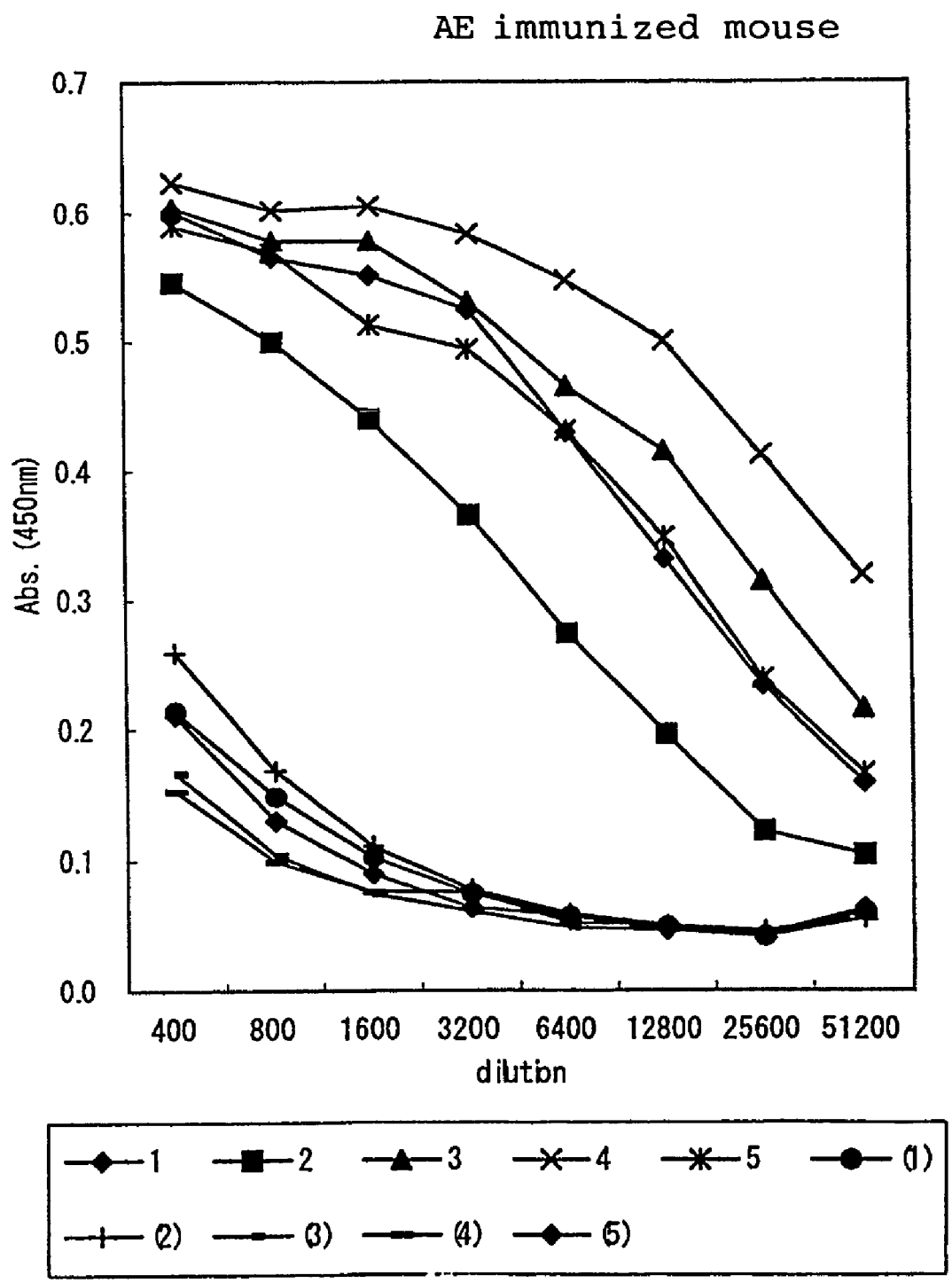

Oishi et al. 1999. Chem. Commun. pp. 2035-2036.*
Oishi et al. 2001. Chem. Commun. pp. 381-382.*
Nagumo et al., Concise Synthesis of Ciguatoxin ABC-Ring Fragments . . . , Bioorganic & Medicinal Chemistry Letters, 2001, vol. 11, No. 15, pp. 2037-2040.
Sasaki et al., Stereocontrolled Synthesis of the JKLM Ring Fragment of Ciguatoxin, Journal of Organic Chemistry, 1999, vol. 64, No. 26, pp. 9399-9415.
Naar et al., Polyclonal and monoclonal antibodies to PbTx-2-type brevetoxins using minute amount of hapten-protein conjugates . . . , Toxicon, 2001, vol. 39, No. 6, pp. 869-878, Abs.Only.
Pauillac et al., Characterization of mice antisera elicited with a ciguatoxin tetracyclic synthetic ring fragment (JKLM) . . . , Toxicon, 2000, vol. 38, No. 5, pp. 669-685, Abs Only.
Hokama et al., A radioimmunoassay for the detection of ciguatoxin, Toxicon, 1977, vol. 15, No. 4, pp. 317-325, Abs Only.
Hokama et al., Cross-reactivity of highly purified okadaic acid (OA) . . . , Journal of Clinical Laboratory Analysis, 1992, vol. 6, No. 1, pp. 54-58, Abs Only.

* cited by examiner

Fig.3

Sandwich ELISA

SANDWICH IMMUNOASSAY KITS FOR DETECTING CIGUATOXIN CTX3C

FIELD OF THE INVENTION

The present invention relates to sandwich immunoassay kits, which are useful for detecting the large non-protein molecule, in particular, ciguatoxins, featuring a use of at least two kinds of monoclonal antibodies, which comprise at least labeled monoclonal antibody, such as enzyme labeled monoclonal antibody and at least one non-labeled monoclonal antibody. Each of them binds specifically to a different part of ciguatoxins to be detected, and was prepared by using a synthetic hapten derived from a different partial structure of ciguatoxin CTX3C.

Further, the present invention relates to hybridoma 3D11 deposited under accession number FMRM PB-8293 producing the monoclonal antibody described above. A protein conjugate with the synthetic hapten was used as the antigen for preparation of the hybridoma 3D11. The present invention also relates to hybridoma 10C9 deposited under accession number FMRM PB-8292 producing the monoclonal antibody described above. A protein conjugate with the different synthetic hapten was used as an antigen for the preparation of the hybridoma 10C9.

BACKGROUND OF THE INVENTION

The investigation of marine toxins by immunoassay, in particular ciguatoxins, was initiated from around 1977 along with the development of radioimmunoassay. Ciguatera poisons can be collected in a trace amounts from nature. For example, from 850 moray eels, namely from 4 tons of moray eels, only 0.35 mg of main poisonous constituent ciguatoxin is collected. And also, since it is difficult to produce ciguatoxin by cultivation, production of antibodies against ciguatoxins has been hampered. Hokama et al. of Hawaii University prepared a protein conjugate by coupling of ciguatoxin (1 μg) with human serum albumin by carbodiimido method and immunized on mice with said conjugate as an antigen, and elicited a monoclonal antibody (Toxicon Vol. 15, 1977, page 317) that bound to ciguatoxin. However, the antibody exhibited strong cross-reactivity with okadaic acid, and the difference of affinity is only about 5 times (Journal of Clinical Laboratory analysis Vol. 6, 1992, page 54). Furthermore, the antibody showed cross-reactivity with brevetoxins, maitotoxin or palytoxin (Journal of AOAC International Vol. 81, 1998, page 727), however, detailed deta has not been reported. A reagent or a kit (Cigua Check TM) for the detection of fishes polluted with ciguatoxins by an immunoassay has been developed utilizing the Hokama's antibody.

At the earlier stage, the inventors of the present invention synthesized ABC ring fragment, the left end of ciguatoxin, and prepared three kinds of monoclonal antibodies using protein conjugate obtained by utilizing the ABC ring fragment as a synthetic hapten, however, these monoclonal antibodies showed very weak affinity to ciguatoxin (Synthesis, 1999, page 1431). Other groups have also examined the immunization of protein conjugates of synthetic hapten (JKLM ring fragment), however, they have not succeed to prepare monoclonal antibody yet (Toxicon Vol. 38, 2000, page 669).

In the above circumstance, the inventors of the present invention have designed and synthesized a synthetic hapten derived from IJKLM ring fragment, which is a partial structure of right end of ciguatoxin CTX3C. The inventors also have established a hybridoma (deposited under the accession number FMRM PB-8293) by immunization of mice with a protein conjugate of the synthetic hapten and thereby have succeeded to produce a monoclonal antibody, which has high specificity to ciguatoxin CTX3C, using said hybridoma. And said monoclonal antibody is named as 3D11 [Deposit date at IPOD (International Patent Organism Depositary), AIST (National Institute of Advanced Industrial Science and Technology) was Mar. 5, 2002 and was deposited by request for transference according to Budapest convention on Feb. 13, 2003 under accession number FMRM PB-8293]. Dissociation constant of said monoclonal antibody 3D11 to ciguatoxin CTX3C is 122 nm. Further, the cross-reactivity of said antibody with structurally related polycyclic ether type marine toxins was investigated. Very weak cross-reactivity of the antibody 3D11 with red-tide toxin brevetoxins was detected, in which the affinity with brevetoxin was less than one $350^{th}$ of the Kd value compared to that with CTX3C.

Further, as the synthetic hapten which is used in order to obtain monoclonal antibody of ciguatoxins, conjugate is synthesized by conjugating the derivative prepared by introducing carboxylic acid linker to C16 site of ABC ring fragment of ciguatoxin with BSA or KLH which are carrier proteins, emulsified the conjugate in RIBI adjuvant and injected the emulsified conjugate to five Balb/c mice for 4 times and immunized these mice, then spleen is picked out from these mice, cells of said spleen are fused with myeloma cells, P3X63-Ag8.653, and obtain said antibody and reaction specificity of the antibody to the synthetic hapten is estimated (Synthesis 1999, No. SI. 1431-1436 ISSN 0039-7881). That is, using ciguatoxins, in particular, partial structure of ciguatoxin CTX3C, study of synthetic hapten using a part of ring fragment of synthetic ciguatoxin used for the production of monoclonal antibody which is useful for the investigation of ciguatoxin CTX3C by immunological method is carried out. Concerning above mentioned study, the inventors of the present invention has continued designing a synthetic hapten through which can be obtained monoclonal antibody whose affinity to ciguatoxin is further improved. Further, since ciguatoxin is a large molecular whose molecule length is approximately 3 nano meter, ABCDE ring fragment, which is the partial structure of left-hand terminus of ciguatoxin, is designed as the hapten and investigated the method for approach for the synthesis. By the method to immunize a mouse with the protein conjugate of this synthetic hapten, above mentioned hybridoma 10C9 deposited under accession number FERM PB-8292 [Deposit date at the IPOD (International Patent Organism Depositary), AIST (National Institute of Advanced Industrial Science and Technology) was Mar. 5, 2002 and was deposited by request for transference according to Budapest convention on Feb. 13, 2003 under accession number FMRM PB-8292] is prepared, and succeeded to produce above mentioned one monoclonal antibody which has high specificity to ciguatoxins using said hybridoma.

The subject of the present invention is basically to provide a kit to detect ciguatoxins by sandwich method whose detective feature is more improved by using combination of two kinds of monoclonal antibodies. Further, for the purpose to accomplish said basic subject, the subject of the present invention is to provide two kinds of hybridomas which produce each monoclonal antibody to obtain said kit, two kinds of synthetic haptens useful to obtain each hybridoma and synthetic hapten-protein conjugates useful to obtain hybridoma which produce said monoclonal antibody prepared by combining the synthetic hapten to carrier protein.

As the first step, for the purpose to produce two kinds of monoclonal antibodies used for the sandwich method, two kinds of novel compounds used as synthetic haptens, one of them having IJKLM ring of composing ciguatoxin CTX3C and the other having ABCDE ring fragment of CTX3C are respectively synthesized.

Then, by immunizing with each protein-hapten product obtained by reacting each synthetic hapten with carrier protein, hybridoma which produce each monoclonal antibody reacting specifically to ciguatoxins CTX3C is obtained. And to one of said monoclonal antibody a labeling compound is bonded and by combining the labeled monoclonal antibody with other non labeled monoclonal antibody, sandwich immunoassay kit which can reduce false positive remarkably can be obtained and the technical concept of said sandwich immunoassay kit is established.

DISCLOSURE OF THE INVENTION

The first one of the present invention is (1) a sandwich immunoassay kit for detecting ciguatoxins, comprising of two monoclonal antibodies that are prepared by using synthetic haptens represented by formula 1 and formula 2, and are produced from hybridoma 3D11 deposited under accession number FMRM PB-8293 and 10C9 deposited under accession number FMRM PB-8292, respectively.

formula 1 formula 2

-continued in above formulae, R is H or methyl group.

Desirably, (2) the first one of the present invention is a sandwich immunoassay kit for detecting ciguatoxins of (1), wherein one of monoclonal antibodies is labeled, further desirably, (3) the first one of the present invention is a sandwich immunoassay kit of (2), wherein the labeling constituent is an enzyme.

(4) The second one of the present invention is a compound represented by above mentioned formula 1.

(5) The third one of the present invention is an use of the compound represented by formula 1 as a synthetic hapten for the development of a hybridoma that produces a monoclonal antibody against ciguatoxins.

(6) The fourth one of the present invention is a monoclonal antibody against ciguatoxins, which is elicited by immunization of a conjugate represented by formula 3 of the synthetic hapten with a carrier protein.

formula 3

In formula 3, n is an integer of 1 or more.

(7) Desirably, the fourth one of the present invention is the monoclonal antibody of (6) elicited by using protein conjugates of synthetic haptens, wherein the carrier protein is bovine serum albumin, keyhole limpet hemocyanin or egg albumin (8) The fifth one of the present invention is hybridoma 3D11 which produces monoclonal antibody against ciguatoxins, which is deposited at IPOD of AIST in Japan under accession number FMRM PB-8293.

(9) The sixth one of the present invention is a compound comprising a diastereomer mixture represented by above mentioned formula 2.

(10) The seventh one of the present invention is a reactive functionality that is capable of conjugation with a carrier protein, which is required for the development of a hybridoma producing a monoclonal antibody against ciguatoxin CTX3C.".

formula 4

In formula 4, —O-L is a leaving group for condensation with a carrier protein.
(11) Desirably, the invention is the novel compound of (10), wherein —O-L is carbodiimide or N-hydroxysuccinimide.
(12) The eighth one of the present invention is protein conjugate represented by general formula 1 prepared by condensation of the compound represented formula 4 with a carrier protein.", general formula 1

In the formula, n is a positive integer of 1 or more.
(13) Desirably the invention is the protein conjugate compound of (12), wherein the carrier protein is bovine serum albumin (BSA), keyhole limpet hemocyanin (KLH) or egg albumin (OVA).
(14) The ninth one of the present invention is a monoclonal antibody against ciguatoxin CTX3C elicited by immunization using the protein conjugate of (13). And,
(15) The tenth one of the present invention is hybridoma 10C9 deposited at IPDO of AIST in Japan under accession number FMRM PB-8292 that produces monoclonal antibody against ciguatoxin CTX3C."

BRIEF ILLUSTRATION OF DRAWINGS

FIG. 1. 1-5 indicate antibody titer of the sera against conjugate AE-BSA prepared by binding A-E ring fragments of ciguatoxin to BSA, (1)-(5) indicate antibody titer of the sera against conjugate IM-BSA prepared by binding I-M ring fragments of ciguatoxin to BSA.

Figure 2:
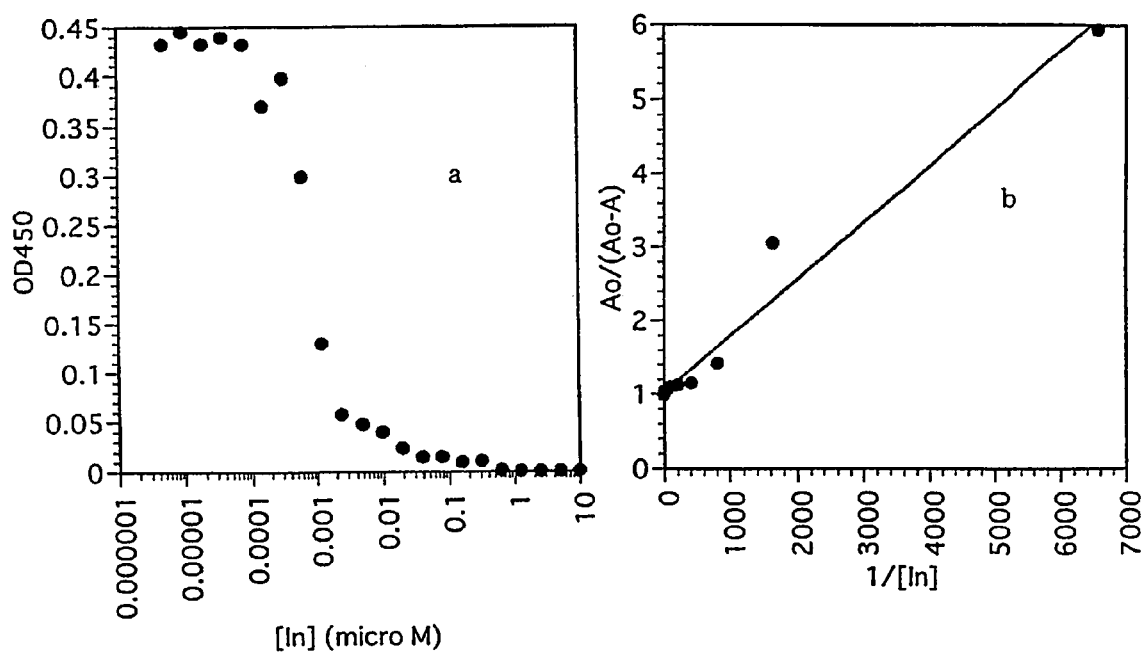

FIG. 2. The drawing of left hand side shows the inhibition data of binding of 10C9 antibody and ABCDE-BSA against adding ABCDE ring fragment (upper) and CTX3C (lower). The drawing of right hand side shows Klotz plotted data of the left drawing, and from the slope of those lines the binding dissociation constant can be calculated.

Figure 3:
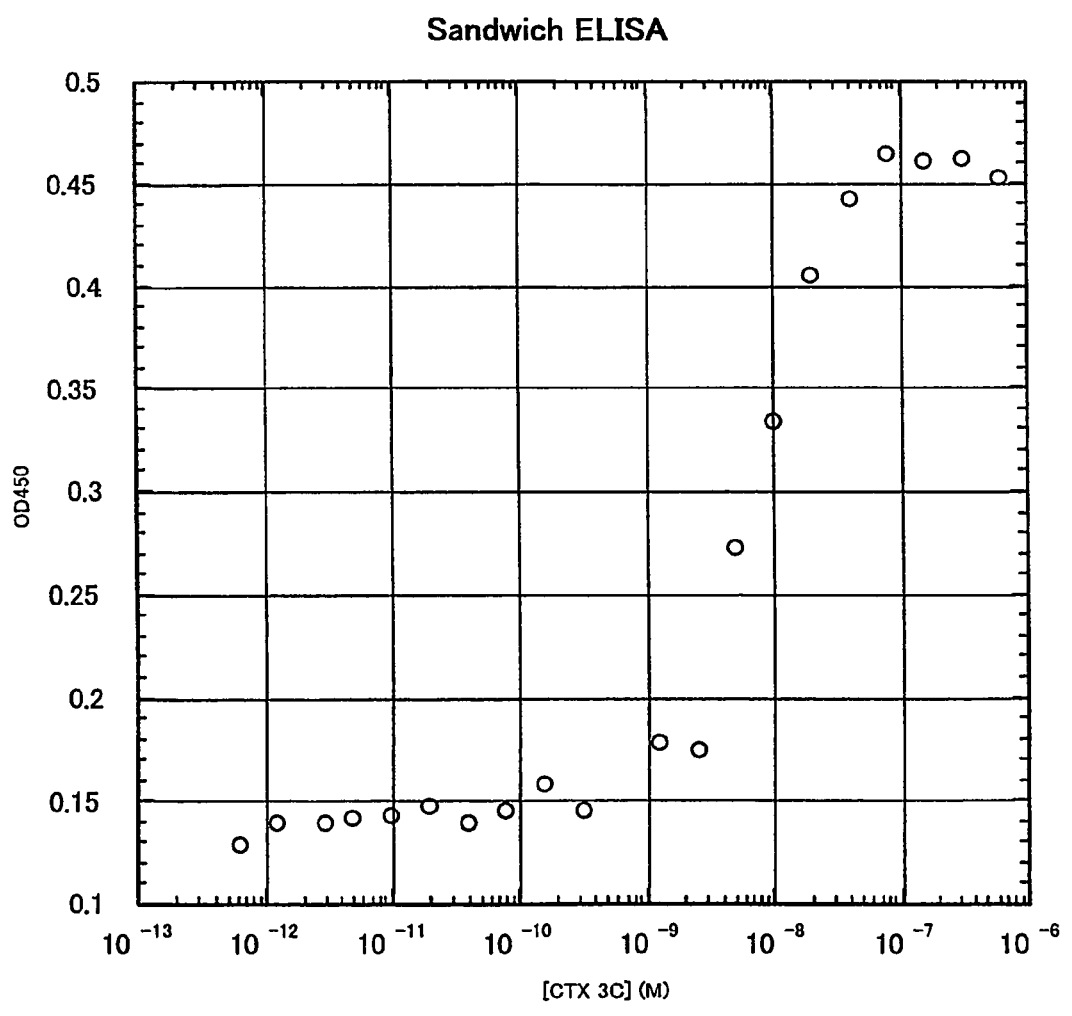

FIG. 3. 50 μL/well of PBS solution of 10C9 (4.3 μg/mL) is poured into ELISA Plate (83590) of Coaster Co., Ltd and stood for one night at 4° C. Solution is thrown away and PBS containing 1% skimmed milk (400 μL/well) is added and stand for one hour at room temperature. Solution is thrown away and after washed by PBS-Tween for three times (200 μL/well), diluted solution of CTX3C (50 μL/well) is added and is stood for one hour. After solution is thrown away, washed by PBS-Tween for 3 times (200 μL/well). PBS-Tween solution of 3D11-HPR (1 μg/mL, 50 μL/well) is added and stand for one hour at room temperature. Solution is thrown away and washed by PBS-Tween for 3 times (200 μL/well), then OPD solution (100 μL/well, Sigma Co., Ltd. FAST (™ o-PHNYLENE DIAMINE DIHYDROCHLORIDE SETS is used) is added and colored for 5-10 minutes at room temperature. 2N sulfuric acid aqueous solution (50 μL/well) is added to stop the reaction and absorbance (450 nm) is measured by Microplate Reader Benchmark of Bio-Rad Co. Ltd. Results are shown.

PREFERRED EMBODYMENT OF THE INVENTION

The present invention will be illustrated more in detail.

A. Establishment of the method of detection for compound which exists trace amount in environment or foods, especially, establishment of the method for precise and accurate detection is strongly required for the safety life. Since the establishment of the method of a sandwich immunoassay for detecting non-protein molecule to be detected using combination of plural monoclonal antibodies which binds specifically to the non-protein molecule to be detected obtained by utilizing plural synthetic haptens derived from partial structure in a molecule which composes the non-protein molecule to be detected of the present invention provides highly precise detection method, said method can be said as an innovational technique.

B. Compound 3 contained in synthetic hapten represented by formula 1 of the present invention can be obtained by following scheme 1. The starting compound 1 for schemata 1 is known (Document; Chem. Comm. 2001, 381-382).

Compound 2 is obtained by following process. Compound 1 (7.8 mg, 11 μmol), ethylacetate (EtOAc) (100 μL), methanol (300 μL) and Pd(OH)$_2$ (20%, on carbon: 1.1 mg, 11 μmol) are put in a 20 mL eggplant-type flask. Under the hydrogen atmosphere (thick balloon is used) the content is stirred for 3 hours at room temperature. After diluted with ethylacetate, filtered through celite. Filtered solution is concentrated and the compound 2 (6.2 mg, 13 μmol) is quantitatively obtained.

Mixture of compound 3 and compound 3' is obtained by following process. Compound 2 (4.2 mg, 9.0 μmol), CH$_2$Cl$_2$ (300 μL), (MeO)$_2$CHCH$_2$CO$_2$Me(25 μL, 180 μmol) and TsOH.H$_2$O (0.5 mg, 3 μmol) are put in a 20 mL eggplant-type flask. After the content is stirred for 1.5 hours at room temperature, toluene (1 mL) is added, vacuumed (120 mbar/hPa) by a rotary evaporator and put back to atmospheric pressure after 1 hour. Diluted with ethylacetate, organic layer is washed with saturated aqueous solution of sodium hydrogencarbonate, water and saturated brine, dried with magnesium sulfate anhydride, filtrated and concentrated. Then, it was purified by silica gel column chromatography and diastereomeric mixture at acetal position (3:3'=3:1) is obtained (4.2 mg, 9.0 μmol, 94%). Property of the mixture of compound 3 and compound 3' is shown as follows.

Property of compound 3;
$^1$H-NMR (500 MHz, CDCl$_3$) δ 0.89 (3H, d, J=6.5 Hz, Me17), 1.03 (3H, d, J=6.0 Hz, Me16), 1.06 (3H, d, J=7.0 Hz, Me5), 1.15 (3H, d, J=7.5 Hz, Me12), 1.39 (1H, brq, J=11.5 Hz, H9ax), 1.50~1.62 (4H, m, H17, H6, H4, H16), 1.77-1.88 (4H, m, H20, H19, H5, H4, H6), 1.92-1.97 (2H, m, H19H20), 2.02 (1H, qdd, J=7.5, 5.0, 3.0 Hz, H12), 2.21 (brdt, J=11.5, 5.0 Hz, H9eq), 2.62 (2H, J=5.0 Hz, O$_2$CHCH$_2$CO$_2$Me) 2.85 (1H, dd, J=9.5, 5.0 Hz, H11), 2.96 (1H, brtd, J=9.5, 3.0 Hz, H7), 3.13 (1H, brddd, J=11.5, 9.5, 5.0 Hz, H8), 3.24 (1H, t, J=9.5 Hz, H15), 3.29 (1H, brtd, J=9.5, 4.5 Hz, H2), 3.32 (1H, t, J=9.5 Hz, H1), 3.41 (1H, brtd, J=9.5, 3.0 Hz, H3), 3.64 (1H, dd, J=9.5, 1.5 Hz, H14), 3.69 (3H, s, OMe), 3.68-3.72 (2H, m, H10, H13), 3.78 (1H, brq, J=7.5 Hz, H21), 3.88 (1H, m, H21), 4.01 (1H, dd, J=9.5, 4.5 Hz, H1), 4.87 (1H, t, J=5.0 Hz, O$_2$CHCH$_2$CO$_2$Me). MALDI-TOF MS: Calcd; C$_{29}$H$_{46}$O$_{10}$Na 577.299 (M+Na$^+$); Found; 577.244.

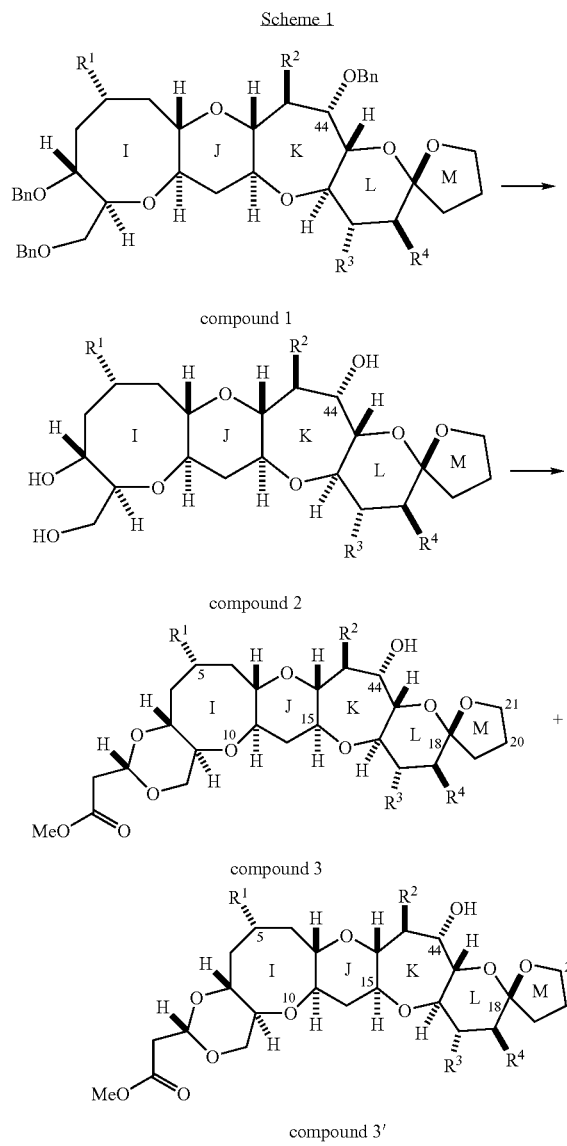

C. Preparation process to protein conjugate is shown in scheme 2.

Synthesis of compound 3, 3'-compound 4, 4';

Compound 3, 3' (4.7 mg, 8.5 μmol), t-BuOH, water (125 μL) and LiOH.H$_2$O (2.8 mg, 68 μmol) are put in a 20 mL eggplant-type flask, and stirred for 1 hour at room temperature. After checking pH (3-4 around), diluted with ethylacetate (10 mL). Dried with magnesium sulfate anhydride, filtered and concentrated, crude compound of 4, 4' is obtained. DMF (200 μL), N-hydroxysuccinimide (9.7 mg, 85 μmol) and EDC.HCl (8.1 mg, 43 μmol) are added and stirred for 12 hours at room temperature. Reaction solution is diluted with ethylacetate (10 mL), organic layer is washed by water for 3 times, dried with sodium sulfate anhydride, concentrated and compound 6, 6' which is activated ester is obtained. The solution to which DMF (100 μL) is added is prepared and used for the preparation of conjugate.

Preparation Of KLH Conjugate;

To the PBS buffer solution (2.0 mL) of KLH (7.0 mg), DMF solution (50 μL) of compound 6, 6' of activated ester (approximately 4.2 μmol) is added and stirred for 10 minutes. After standing for one day, the solution is dialyzed at 4° C. After that, PBS buffer (700 mL) is changed after 14 and 19 hours, and after 28 hours, transferred from dialysis membrane to Eppendolf tube and preserved at −78° C.

Preparation of BSA Conjugate

To the PBS buffer solution (2.0 mL) of BSA (7.0 mg), DMF solution (50 μL) of compound 6, 6' of activated ester (approximately 4.2 μmol) is added and stirred for 10 minutes. After standing for one day, the solution is dialyzed at 4° C. After that, PBS buffer (700 mL) is changed after 14 and 19 hours, and after 28 hours, transferred from dialysis membrane to Eppendolf tube and preserved at −78° C.

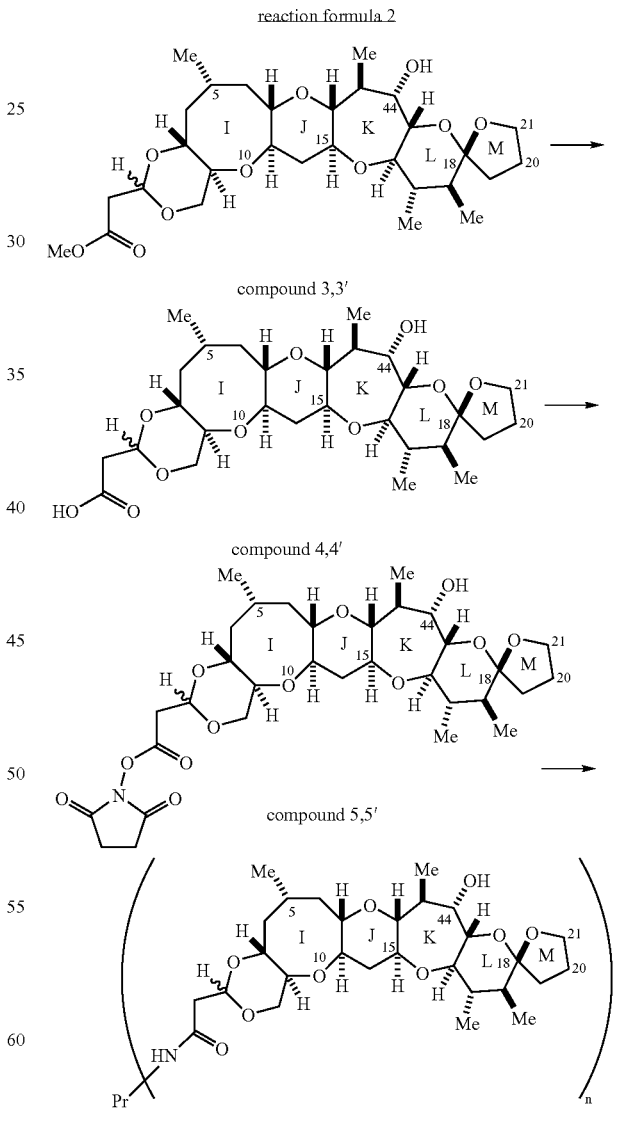

Pr is carrier protein. N is integer of 1 or more.

Analysis of Hapten Conjugate;

BSA conjugate obtained by dialysis is analyzed by mass spectrometric analysis using MALDI-TOF-MS. Average molecular weight of BSA conjugate is approximately 71800 (average molecular weight of BSA is approximately 66400). Since molecular weight of hapten is 540, it is understood that 10 haptens (mean value of n in compound 6, 6') are connected to the BSA conjugate in average.

D. Preparation of Monoclonal Antibody;

To IJKIM-KLH (10 μg) obtained as above, RIBI adjuvant (RIBI Immunol. Product of Res. Inst. Co., Ltd.) is added and stirred well to form emulsion, then said emulsion is given intraperitoneally to Balb/c mice (five mice) 3 times every 2 weeks. On day 35 after the first immunization, sera of these mice are collected and antibody titer of serum is titrated by ELISA method, using IJKLM-BSA, formula 5.

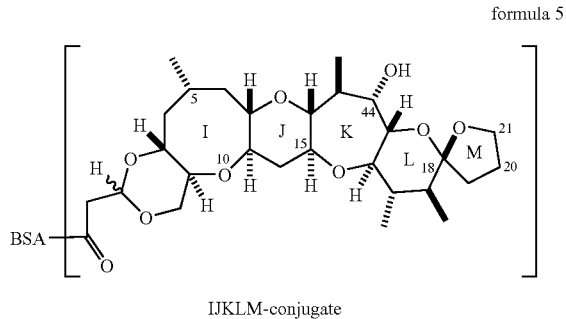

IJKLM-conjugate formula 5

E. Measurement of Antibody Titer by ELISA Method

50 μL of IJKLM-BSA solution was put into each well of plate for 96 well ELISA (product of FALCON, 3910) and left for 2 hours at room temperature, further kept for one night at 4° C., so as for the conjugate to be adsorbed to the plate. The plate was washed by PBS-Tween for 3 times [5% Tween 20 (made by Wako Junyaku Co., Ltd., polyoxyethylene (20) sorbitan monolaurate) or No. 167-11515, made by ICI, corresponding to Tween 20 was put into PBS buffer] then washed by MILLI-Q water once and un-adsorbed conjugates was removed. The supernatants cultured hybridomas or antiserum, purified antibody solution were added and left for 1 hour at room temperature, then washed by PBS-Tween and MILLI-Q water. Enzyme labeled secondary antibody (goat anti-mouse IgG-horseradish peroxidase: HRP) (62-6520; product of ZYMED, 1000 times diluted) was put into each well, left 1 hour at room temperature and washed by PBS-Tween and MILLI-Q water. 100 μL of substrate solution [the contents of the substrate solution: 4.0 mg of 1,2-phenylenediamine, 10 μL of hydrogen peroxide aqueous solution, 10 ml of 0.1 M citric acid buffer (pH 5.0)] was added and processed for color reaction for 5 minutes, then the reaction was stopped by adding 2N sulfuric acid (50 μL). Using a micro plate absorbancy measuring apparatus (BIO-RAD, Benchmark 170-6850), absorbance at 450 nm is measured and positive clone was judged.

Measurement of Antibody Titer in Serum;

50 μL of PBS buffer was put into upper most stage of 96-well ELISA plate which IJKLM-BSA solution was adsorbed. Antiserum of mouse (50 μL) diluted at 200 times was added to the upper most well (A1), then the two fold dilution of this solution was done in order and made from 400 times to 51200 times dilution in column A1-A8 in tandem. After the plate was left for 1 hour at room temperature, and absorbance at 450 nm was measured by above mentioned method. By plotting logarithms of serum dilution rates (abscissa) and absorbance (OD, ordinate), sigmoid titration curve was obtained, and it became clear that the antibodies in serum bond with IJKLM-BSA conjugate depending on the concentration of serum. Further, it was confirmed that the antibodies in serum did not bind to ABC-BSA at all.

Among the five mice, the mouse which shows the highest antibody titer was selected. The selected mouse was supplementary immunized intraperitoneally with IJKLM-KLH (100 μg) and after 3 days spleen was picked out from the mouse. Fragments of tissue or organ sticking to the spleen were removed using forceps and the spleen was transferred to a petri dish added basal medium [RPMI Medium 1640 (made by GIBCO, 1 bag), 2 g of sodium hydrogencarbonate, 20 g of penicillin-streptomycin (made by GIBCO) and 20 mL of 200 mM-glutamine were dissolved in distilled water to prepare a 1000 mL solution with pH 7.2] and the cells in the spleen were suspended using forceps. The spleen cells suspended liquid was filtered and transferred to a 50 mL centrifuge tube and furthermore 15 mL of the basal medium was added, pipetted well and filtered to prepare the total volume 30 mL of cell suspension. Centrifuged at 800 r.p.m. for 5 minutes at room temperature and supernatant was removed and tapped. 30 mL of HT-BC medium [mixture of 200 ml of bovine fetus serum (FCS), 20 mL of HT (product of COSMO BIO, HT solution (50 times concentrated), 50 mL of BC (Briclone, product of Bioresearch Island) and 730 mL of base medium] was added and the cells were suspended.

Preparation of Hybridoma;

A frozen tube of myeloma cells [P3X63-Ag 8.563 (product of Dainihon Seiyaku)] was took out from the refrigerator (−130° C.) and rapidly defrosted in a 37° C. incubator. After the tube was sterilized with alcohol cotton, cell suspension in the tube was transferred to 30 mL of basal medium. Centrifuged at 800 r.p.m. for 5 minutes at room temperature and supernatant was removed then tapped. 10 mL of 10 FCS medium (prepared by adding 10% FCS to the base medium) was added and prepared the cell suspension, then transferred to a 50 mL culture flask. A cap of the flask was loosen and the flask was placed in $CO_2$-incubator. Subcultured every 1-2 days and the volume was brought to 2 bottles of 250 mL flasks (90- 100 mL).

Spleen cells ($2 \times 10^8$ cells) obtained from mouse and myeloma cells ($5 \times 10^7$ cells) were mixed and centrifuged at 800 r.p.m. for 5 minutes at room temperature. Then supernatant was removed and tapped. After that, 30 mL of ECF buffer [prepared by dissolving 45.5 g of mannitol, 10 mM calcium chloride (10 mL), 10 mM magnesium chloride (10 mL) and 20 mM tris buffer <tris(hydroxymethyl)aminomethane> (10 mL) dissolved in distilled water to make 1000 mL solution with pH 7.2] was added, the -supernatant was removed and tapped. After these procedures were repeated for 2 times, then ECF buffer (4.8 mL) was added.

1.2 mL each of this solution was pipetted into 6 well plates (made by SUMIRON) and cells was fused using SSH-10 cell fusion apparatus (made by Shimazu) by following conditions [distance between electrodes: 1.0 mm, alternating current frequency: 1 MHz, alternating current initial stage applied voltag: 80V, alternating current initial stage applied time: 10 s, pulse duration: 40 μs, pulse voltage: 920V, pulse electric field strength: 2.30 kV/cm, secondary applied alternating current voltage: 80V, applied pulse interval: 1.0 s; applied numbers of pulse: 1, pulse voltage change: +0V, last alternating current applied time: 10 s, AC voltage damping factor: 0%, contact strengthening: off.

Hybridoma cells prepared above was transferred to 10 plates of 96-well plate, in which 100 μL of HAT culture medium (selective medium) [the mixture composed of 110 mL of base culture medium, 30 mL of FCS, 7.5 mL of BC and HAT (50 times concentrated solution of HAT, which is the product of Cosmo Bio Co., Ltd.)] was contained. After two weeks, hybridomas which produce the antibody that binds to IJKLM ring fragment of the hapten, were screened using IJKLM-BSA by the ELISA method. After positive wells were selected, and cloned two times, then the positive clones that were confirmed to produce the antibody in repeated ELIZA were cultivated successively to proliferate to produce about 200 mL of the cell suspension respectively. Consequently, following three kinds of monoclonal antibody, whose immunogen was IJKLM-KLM, could be prepared. That was, one was IM (means to have a ring of from I to M) -3D11 produces from the hybridoma, which was primary deposited at IPOD (International Patent Organism Depositary) of AIST (National Institute of Advanced Industrial Science and Technology, in Japan) under access number FERM P-18750 and was transferred by request according to Budapest convention on February 13, and deposited at IPOD of AIST on Feb. 2, 2003 under accession number FERM PB-8293, and the the name of the antidody was same to the name of the deposited hybridoma, and other ones were IM-2C7 and IM-8B12. The binding test of the obtained monoclonal antibodies were carried out using ELISA method. As antigens, the BSA conjugate, which were coupled with the partial structure of ciguatoxins, that were ABC, ABCD, A*BC (means A ring fragment is ciguatoxin type) and IJKLM ring structure were used. From the results, as an antibody having strong affinity to the IJKLM ring fragment, IgG antibody IM-3D-11 was selected. Dissociation constant Kd for IJKLM was 8.6 nM (details regarding to the method for measurement describe later).

Purification of Antibody and Determination of Subclass;

Supernatants were purified using the anti-mouse IgG+IgM affinity columns (product of NFG Industries, Ltd.) [phosphoric acid buffer for bonding (pH 7.0) and buffer for elution (0.2M Glycine-HCl, pH 2.5)]. The purified antibody was confirmed to be >95% in purity by the SDS-PAGE analysis (sodium dodecyl sulfate-acrylamide gel electrophoresis). The subclass of these antibodies were determined using a typing kit (37501) made by PIERCE Co., Ltd.

Analysis of Affinity of Antibody (Experiment or Competitive Inhibition);

Selected three monoclonal antibodies mentioned above, namely IM-3D11, IM-2C7 and IM-8B12, were purified and the dissociation constant (Kd) with hapten was determined. The solution of a serial two-fold dilution of a competitive inhibitor (each 30 μL of PBS solution) was prepared in plates for ELISA (from A1 to A12 well) in order. Antibody solution (30 μL) was added to each plates and left for 2 hours at room temperature. 50 μL of the mixed solution of the antibody and the inhibitor was added to 96-well ELISA plate to which hapten-BSA solution was absorbed (refer to affinity analysis of antibody), and left for 20 minutes at room temperature. After the plates were washed, absorbance was measured and the titration curve was obtained. Referring to the method of Friguet et al. [Journal of Immunological Method, vol. 77 (1985), page 305], Kd value of the inhibitor was determined from the slope of the straight line obtained by the Klotz plotting. From the results, IM-3D11 was found to show a high affinity (Kd=8.6 nM) to IJKLM ring fragment (IM) (formula 6).

formula 6

Along with said results, the binding test with toxin's main body CTX3C was examined using the above mentioned experimental system for competitive inhibition. IM-3D11 bound strongly to CTX3C (Kd=122 nM). Further, as for IM-3D11, the binding test with marine polyether toxin whose structure is similar was examined, however, bound scarcely with Okadaic acid or Maitotoxin. The cross reactivity with red-tide toxin brevetoxins was detected, however, compared the affinity to CTX3C, the former was approximately one 350th (BTXA: Kd=350 μM) and was very weak.

Enzyme Labeling Method of 3D11 Antibody [Synthesis of 3D11-HRP (Horseradish Peroxitase)] (For Sandwich Method);

HRP labeling of 3D11 antibody was carried out by following an explanatory note of Pierce Co., Ltd., using EZ-Link (™ Plus Activated Peroxitase and kit. 1 mg of aqueous solution (100 μL) of EZ-Link Plus Activated Peroxide was added to carbonate-bicarbonate buffer solution (10 mL) of 3D11 antibody (1 mg), and developed the reaction for 1 hour at room temperature. 10 μL of Reductant solution (NaBH$_3$CN is main reagent) was added to the reaction mixture and left for 15 minutes at room temperature. 20 mL of Quench buffer was added and the obtained solution was left for 15 minutes at room temperature. The reaction solution was dialyzed in 1 LPBS for 3 times, then 1 mL of glycerol was added and was preserved at −20° C.

As the other labeling components, the known labeling components can be used.

Illustration of the preparation of the monoclonal antibody to be combined with the labeled monoclonal antibody which has ring fragment A-E (can be abbreviated as AE) of ciguatoxin;

1. Synthesis of diastereomer of above mentioned formula 2 to be synthetic hapten, and mixture of formula 1 and 2 at process 1; Can be obtained by following process 1.

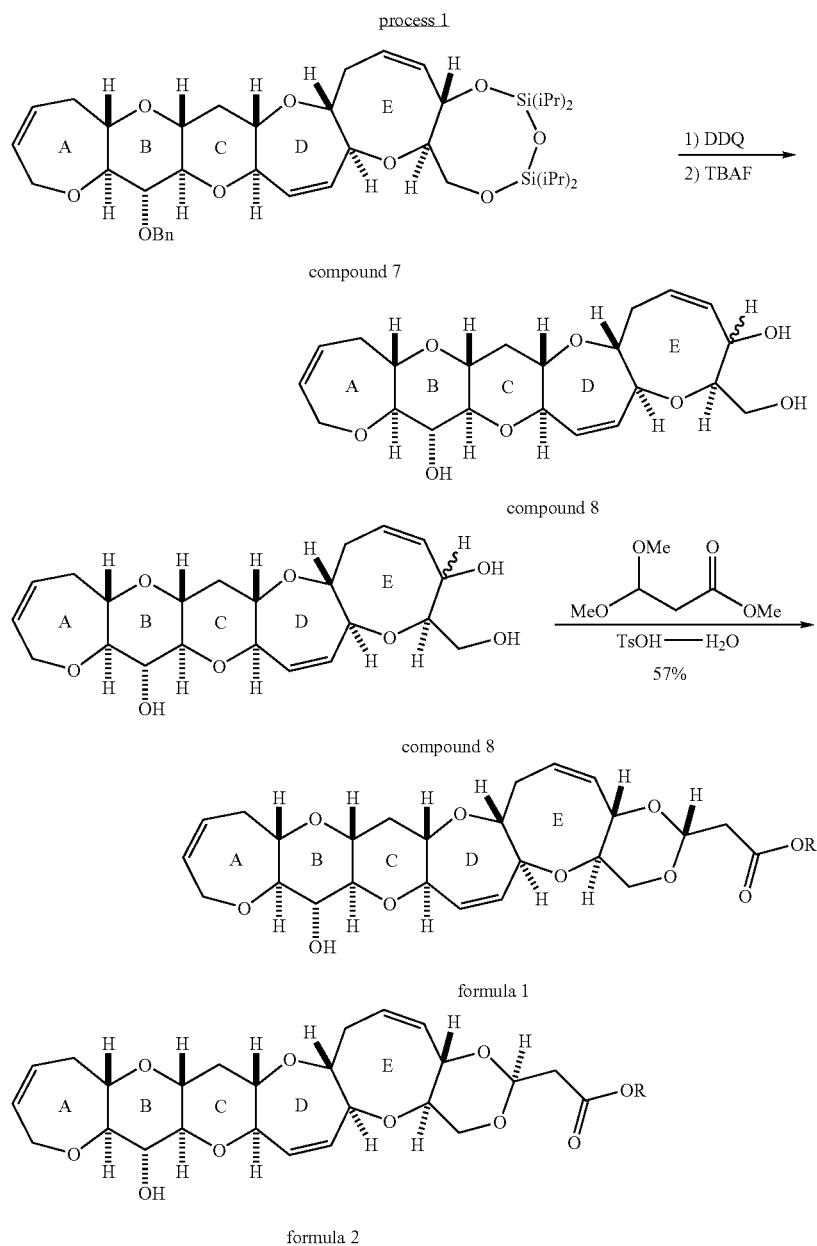

The method for synthesis of the compound of the OH group of compound 7 protected with benzyl group (Bn) was disclosed in M. Maruyama et al, Heterocycles, 2001, 54, 93-99. Compound 8 can be obtained by deprotection of Bn of the compound mentioned in the Document 2 using DDQ (2,3-dichloro-5,6-dicyano-1,4-benzoquinone)(step 1)), and the alcohol compound (4.0 mg, 6.0 μmol) obtained in the step 1) was dissolved in THF (tetrahydrofuran) (2 mL) and tetrabutylammoniumfluoride (TBAF, 1M THF solution: 1.8 μL, 18 μmol) was added at room temperature(step 2)). After 30 minutes reaction the solution was concentrated, purified by silica gel chromatography. The compound 8 (2.5 mg, 5.9 μmol, 98%) was obtained.

Compound 8 (2.8 mg, 6.6 μmol), CH$_2$Cl$_2$ (300 μL), (MeO)$_2$CHCH$_2$COOMe (10 μL, 70 μmol) and TsOH.H$_2$O (0.5 mg, 3 μmol) were put in a 20 mL egg plant type flask. After stirred for 1.5 hours at room temperature, toluene (1 m) was added and vacuumed by a rotary evaporator (120 mbar/hPa) and put back to the atmospheric pressure after 1 hour. Purified by silica gel chromatography and 1.9 mg (3.8 μmol) of diastereomer mixture regarding acetal site, compound of formula 1 of process 1: compound of formula 2=2:1 was obtained in 57%. The property of mixture of compounds of formula 1 and formula 2 of process 1 are shown below.

The property of mixture of compounds of formula 1 and formula 2 of process 1;

$^1$H-NMR (500 MHz, CDCl$_3$) δ 1.53 (1H, m, H10ax), 2.28 (1H, dt, J=12.0, 4.5 Hz, H10eq), 2.32 (1H, m, H17), 2.37 (1H, m, H4), 2.62 (1H, m, H4), 2.64 (1H, m, H17), 2.67 (1H, dd, J=15.5, 5.5 Hz, H24), 2.69 (1H, dd, J=15.5, 5.5 Hz, H24), 3.01 (1H, t, J=9.0 Hz, H8), 3.11 (1H, ddd, J=11.0, 9.0, 4.5 Hz, H9), 3.22-3.26 (2H, m, H5, H11), 3.34 (1H, m, H21), 3.43 (1H, t, J=10.5 Hz, H22), 3.58-3.64 (3H, m, H16, H7, H6), 3.70 (3H, s, OMe), 3.80 (1H, ddd, J=9.0, 4.0, 2.5 Hz, H12), 4.02 (1H, ddt, J=15.0, 4.0, 2.5 Hz, H1), 4.11 (1H, dd, J=10.5, 5.5 Hz, H22), 4.12 (1H, m, H15), 4.24 (1H, m, H20), 4.32 (1H, dd, J=15.0, 6.0 Hz, H1), 4.93 (1H, t, J=5.5 Hz, H23), 5.63 (1H, brdt, J=12.5, 2.5 Hz, H14), 5.70 (1H, m, H13), 5.73 (1H, dd, J=10.5, 5.0 Hz, H19), 5.80 (1H, m, H18), 5.83 (1H, m, H3), 5.92 (1H, m, H2).MALDI-TOF MS: Calcd for $C_{26}H_{34}O_{10}Na$ 529.205 (M+Na$^+$); Found 529.185.

Compound 8 of process 2 was obtained by converting R of compounds of formula 1 and 2 in the process 1 to H by treating the compounds of formulae 1 and 2 with LiOH. The compound shown by the formula 4, wherein L was succinimide, of compound 9 can be obtained by following process 2.

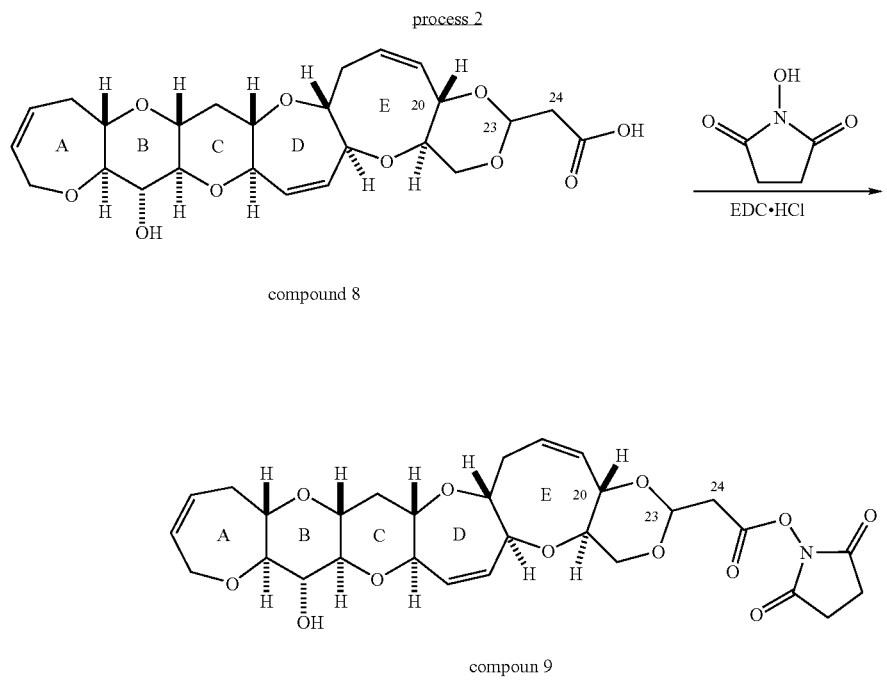

Compound of formula 1 and 2 in the process 1 (2.5 mg, 4.9 μL), t-BuOH (0.5 mL), water (125 μL) and LiOH.H$_2$O (2.8 mg, 68 mol) were added and stirred for 1 hour at room temperature. KHSO$_4$ (18.6 mg, 136 μmol) was added and after the pH of solution (3-4 around) was confirmed, diluted with ethyl acetate (40 mL). Dried by magnesium sulfate anhydride, filtered and concentrated and crude compound 8 of process 2 was obtained. To the obtained crude compound 8 of process 2, DMF (DMF=N,N-dimethylformamide, 200 μL), N-hydroxy succinimide (5.6 mg, 4.9 μmol) and 4.8 mg (25 μmol) of EDC-HCl (EDC=1-(3-dimethylaminopropyl-3-ethylcarbodiimide) were added and stirred for 12 hours at room temperature. Reaction solution was diluted with ethylacetate (40 mL), organic layer was washed by water for 3 times. Dried by magnesium sulfate anhydride and concentrated, then compound 9 of process 2, which was activated ester, was obtained. The solution added with DMF (100 μL) was prepared and used for the preparation of the conjugate.

2. Preparation of Protein Conjugate;

Preparation of KLH conjugate;

To the PBS buffer solution (1.0 mL) of KLH (5.0 mg), DMF solution (50 μL) of compound 9 (approximately 2.4 μmol), which was activated ester, was added and stirred for 10 minutes. After left for one day, the solution was dialyzed at 40° C. PBS buffer (700 mL) was changed after 5.9 hours, and after 12 hours transferred from dialysis membrane to Eppendolf tube and preserved at −78° C.

Preparation of BSA Conjugate

To the PBS buffer solution (2.0 mL) of BSA (7.0 mg), DMF solution (50 μL) of compound 9 (approximately 2.4 μmol), which was activated ester, was added and stirred for 10 minutes. After left for one day, the solution was dialyzed at 4° C. PBS buffer (700 mL) is changed after 5.9 hours, and after 12 hours transferred from dialysis membrane to Eppendolf tube and preserved at −78° C.

3. Analysis of Haptenic Titer;

BSA conjugate obtained by dialysis was analyzed by mass spectrometric analysis using MALDI-TOF-MS. Average molecular weight of BSA conjugate was approximately 70200 (average molecular weight of BSA is approximately 66400). Since molecular weight of hapten was 476, it was confirmed that 8 haptens are connected to the BSA conjugate in average.

4. Preparation of Monoclonal Antibody (to be Used as a Non Labeled Antibody);

To ABCDE-KLH (100 μg) obtained as above, RIBI adjuvant (RIBI Immunol. Product of Res. Inst. Co., Ltd.) was added and stirred well so as to form emulsion, then said emulsion was given intraperitoneally to Balb/c mice (five) 3 times every 2 weeks. On day 39 after the first immunization, sera of these mice were collected and antibody titers of the sera were titrated by the ELISA method using ABCDE-BSA.

ELISA Method;

Into each well of 96-well plates 50 μL of ABCDE-BSA solution was put for ELISA (product of FALCON, 3910) and left for 2 hours at room temperature, and further left for overnight at 4° C., so as for the conjugate to be adsorbed to the plate. The plate was washed by PBS-Tween 3 times [5% Tween 20 (product of Wako Junyaku Co., Ltd., polyoxyethylene (20) sorbitan monolaurate made by the ICI or No. 167-11515 corresponding to Tween 20) is contained to PBS buffer], then washed by MILLI-Q water once and the unadsorbed conjugate was removed. The supernatant of cultured hybridoma or antiserum, purified antibody solution were added and left for 1 hour at room temperature, then washed by PBS-Tween and MILLI-Q water. Enzyme labeled secondary antibody (goat anti-mouse IgG-West horseradish peroxitase: HRP) (62-6520; made by ZYMED,1000 times diluted)was put into each well, left 1 hour at room temperature and washed by PBS-Tween and MILLI-Q water. 100 μL of substrate solution [contents of the substrate solution: 4.0 mg of 1,2-phenylenediamine, 10 μL of hydrogen peroxide aqueous solution, 10 ml of 0.1M citric acid buffer (pH 5.0)] was added and progressed the color reaction for 5 minutes, then stopped the reaction by adding 2N sulfuric acid (50 μL). Using a micro plate absorbancy measuring apparatus (BIO-RAD, Benchmark 170-6850), absorbance at 450 nm was measured and positive clone was judged.

Measurement of Antibody Titer in Serum;

50 μL of PBS buffer was put in the upper most stage of each 96 well plate for ELISA to which hapten (ABCDE or IJKLM)-BSA solution was adsorbed. Antiserum of mouse (50 μL) which was diluted at 200 times was added to the well (A1) of the upper most stage, then the two-fold dilution of this solution was done in order (from 400 times to 51200 times diluted series were prepared in tandem A1-A8). After the plate was left for 1 hour at room temperature, and absorbance at 450 nm was measured by above mentioned method (refer to FIG. 3). By plotting logarithms of serum dilution rate and absorbance, it was found that the antibodies in serum bound with ABCDE-BSA conjugate depending on the concentration of serum.

5. Picking the Spleen out from the Mouse with High Antibody Titer, Cultivation;

The mouse which showed the highest antibody titer was supplementary immunized by giving ABCDE-KLH (100 μg) intraperitoneally, and after 3 days the spleen was picked out from the mouse. Fragments of tissue or organ sticking to the spleen are removed by a forceps and the spleen was transferred to a Petri dish in which basal medium [RPMI Medium 1640 (product of GIBCO, 1 bag), 2 g of sodium hydrogencarbonate, 20 g of penicillin-streptomycin (product of GIBCO) and 20 mL of 200 mM-glutamine were dissolved in distilled water to prepare a 1000 mL solution with pH 7.2 adjusted] was contained and cells in spleen were suspended using forceps. After the spleen cells suspended liquid was filtered, transferred to a 50 mL centrifuge tube and further 15 mL of basal medium was added, pipetted well and filtrated to afford the 30 mL of cell suspension. Centrifuged at 800 r.p.m. for 5 minutes at room temperature and supernatant was removed and tapped. 30 mL of HT-BC medium [mixture of 200 ml of bovine fetus serum (FCS), 20 mL of HT (product of COSMO BIO, HT solution (50 times concentrated), 50 mL of BC (Briclone, product of Bioresearch Island) and 730 mL of basal medium] was added and prepared the cell suspension.

A frozen tube of myeloma cells [P3X63-Ag 8.563 (product of Dainihon Seiyaku)] was took out from a refrigerator (−130° C.) and was thawed in an 37° C. incubator rapidly. After the tube was sterilized with alcohol cotton, the cell suspension in the tube was transferred to 30 mL of basal medium. Centrifuged at 800 r.p.m. for 5 minutes at room temperature and supernatant was removed then tapped. 10 mL of 10 FCS medium (prepared by adding 10% FCS to the basal medium) was added and prepared the cell suspension, then transferred to a 50 mL culture flask. The plug of the flask was loosen and was put in a $CO_2$-incubator. It was subcultured every 1.2 days, and divided into two 250 mL flasks (90-100 mL).

The splenic cells ($2\times10^8$ cells) took out from mouse and myeloma cells ($5\times10^7$ cells) were mixed and centrifuged at 800 r.p.m. for 5 minutes at room temperature. Then supernatant was removed and tapped. After that, 30 mL of ECF buffer [prepared by dissolving 45.5 g of mannitol, 10 mM calcium chloride (10 mL), 10 mM magnesium chloride (10 mL) and 20 mM tris buffer <tris(hydroxymethyl)aminomethane> (10 mL) with pH of 7.2 were dissolved in distilled water to make 1000 mL] was added, supernatant was removed and tapped. After these procedures were repeated for twice, then ECF buffer (4.8 mL) is added.

1.2 mL each of this solution was pipetted into 6 well plate (made by SUMIRON) and cells were fused by following condition using SSH-10 cell fusion apparatus (product of Shimadzu) [distance between electrodes: 1.0 mm, alternating current frequency: 1 MHz, alternating current initial stage applied voltage: 80V, alternating current initial stage applied time of: 10 s, pulse duration: 40 μs, pulse voltage: 920V, pulse electric field strength 2.30 kV/cm, secondary applied alternating current voltage: 80V, applied pulse interval: 1.0 s; applied number of pulse: 1, pulse voltage change: +0V, last alternating current applied time: 10 s, AC voltage damping factor: 0%, contact strengthening: off].

Hybridoma cells prepared above was transferred to each well of 10 plates of a 96-well plate, in which 100 μL of HAT medium [containing HAT-RPMI 1640, 20% FCS, 5% Briclone (made by BioResearch Ireland Co., Ltd.)] After two weeks, hybridomas were screened by ELISA method using ABCDE-BSA. Positive wells were selected, cloned two times, then positive monoclones that were confirmed to produce the antibody in the repeated ELISA were cultivate successively to proliferate to be about 200 mL respectively. Consequently, following six kinds of monoclonal antibody including 10C9 (primary deposited at IPOD of AIST under access number FERM P-18749, on Mar. 5, 2002, and deposited at IPOD of AIST under access number FERM PB-8292, by request for transference according to Budapest convention, on Feb. 13, 2003) could be prepared (Table 1).

TABLE 1

| monoclonal antibody | Kd (nM) vs AE hapten | Kd (nM) vs CTX3C |
| --- | --- | --- |
| 1C5 | 3.1 | 3.1 |
| 2G5 | 7.3 | 23.2 |
| 5E6 | 10.8 | 19.8 |
| 6D5 | 10.0 | 16.2 |
| 10C6 | 10.8 | 26.7 |
| 10C9 | 0.8 | 2.8 |

The binding test of the obtained monoclonal antibody was examined by using ELISA method. As an antigen, BSA conjugate which bound a partial structure of ciguatoxins was used. From the results of examinations, it was found that IgG antidody obtained by immunizing ABCDE-KLM ring fragment bound strongly with ABCDE-BSA (chemical formula) and did not bind with IJKLM-BSA (compound IJKLM-BSA).

compound IJKLM-BSA

Evaluation of The Preparation of Monoclonal Antibody Purification of Antibody and Determination of Subclass;

competitive inhibitor (PBS solution, each 30 μL) was prepared in the plates for ELISA. The antibody solution (30 μL) was added to each plates and left for 2 hours at room temperature. 50 μL of the mixed solution of the antibody and the inhibitor was added to each well of 96-well ELISA plate (product of FALCON, 3910) to which hapten-BSA solution was adsorbed (0.625 μ/mL), and left for 15 minutes at room temperature. After the plates were washed, the absorbance was measured and the titration curve was obtained. Following the method of Friguet et al. [Journal of Immunological Method, vol. 77 (1985), page 305], Kd value of the inhibitor was measured and from the slope of the straight line obtained by Klotz plotting (incline of FIG. 2b).

From the results, it was found that every six monoclonal antibodies of Table 1 bound strongly with ABCDE [can be shortened to AE. ABCDE ring fragment (upper compound of compound 6) and CTX3C (lower compound of compound 6)] (Kd<27 nm). Further, it was found that among 6 antibodies, 10C9 had the strongest affinity to ABCDE ring fragment (Kd=2.8 nM) and also to CTX3C (Kd=2.8 nM). Kd values of each monoclonal antibodies were shown in Table 1.

compound 6

ABCDE ring part

CTX3C

The supernatant liquid was purified by using the anti-mouse IgG+IgM affinity column (made by NGK Industries, Ltd.) [phosphoric acid buffer for binding (pH 7.0) and a buffer for elusion (0.2M Glycine-HCl, pH 2.5)]. The purified antibody was analyzed by SDS-PAGE (sodium dodecyl sulfate-acrylamide gel electrophoresis) and was confirmed that the purified liquid had >95% in purity. The subclass of each antibodies were determined using a typing kit (37501), product of PIERCE Co., Ltd.

Analysis of affinity of antibody (experiment for competitive inhibition); Next, the selected six monoclonal antibodies were purified and the dissociation constant (Kd) for hapten was measured. The solution of serial two-fold dilution of Further, it was found that the binding affinity of antibody reduces remarkably along with the shortening of ABC ring fragment and molecular size (compound 7)(Kd value becomes bigger). Results were summarized in Table 2.

TABLE 2

| monoclonal antibody | Kd (nM) vs AE hapten | Kd (nM) vs AD hapten | Kd (nM) vs AC hapten |
|---|---|---|---|
| 1C5 | 3.1 | 0.68 | 42.4 |
| 2G5 | 7.3 | 0.67 | 11.1 |
| 5E6 | 10.8 | 0.75 | 53.6 |

TABLE 2-continued

| monoclonal antibody | Kd (nM) vs AE hapten | Kd (nM) vs AD hapten | Kd (nM) vs AC hapten |
|---|---|---|---|
| 6D5 | 10.0 | 0.84 | 10.0 |
| 10C6 | 10.8 | 1.1 | 64.6 |
| 10C9 | 0.8 | 1.8 | 73.6 |

AE

AD

TABLE 2-continued

| monoclonal antibody | Kd (nM) vs AE hapten | Kd (nM) vs AD hapten | Kd (nM) vs AC hapten |
|---|---|---|---|

AD compound 7

Further, the binding test with marine polyether toxin whose structure was similar was examined, it was found that it did not bind with red tide toxin [Brevetoxin A (BTX A) and Brevetoxin B (BTX B)], bound with Okadaic acid or Maitotoxin (regarding to the chemical structure of these compound, refer to compound 8) scarcely. Results were summarized in Table 3.

TABLE 3

| monoclonal antibody | BTXA | BTXB | Okadaic acid | Maitotoxin |
|---|---|---|---|---|
| 1C5 | >100 μM | >50 μM | >100 μM | >25 μM |
| 2G5 | >100 μM | >50 μM | >100 μM | >25 μM |
| 5E6 | >100 μM | >50 μM | >100 μM | >25 μM |
| 6D5 | >100 μM | >50 μM | >100 μM | >25 μM |
| 10C6 | >100 μM | >50 μM | >100 μM | >25 μM |
| 10C9 | >100 μM | >50 μM | >100 μM | >25 μM |

Structure of Polycyclicether Type Marine Toxin compound 8

Brevetoxin A (BTXA)

-continued

Brevetoxin B (BTXB)

Okadaic acid

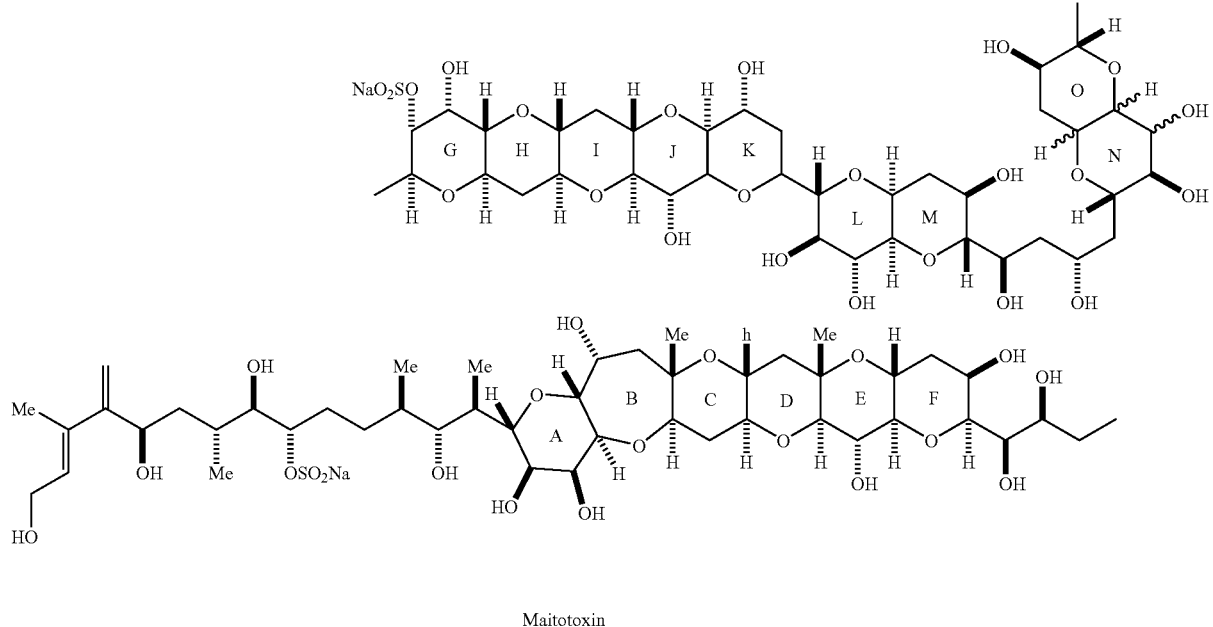

Maitotoxin

Sandwich Detective Method;

50 μL/well of PBS solution of 10C9 (4.3 μg/mL) was put into ELSA Plate (83590) of Coaster Co., Ltd and left for overnight at 4° C. Solution was thrown away and PBS containing 1% skimmed milk (400 μL/well) was added and left for one hour at room temperature. The solution was thrown away and after washed by PBS-Tween three times (200 μL/well), the diluted solution of CTX3C (50 μL/well) was added and left for 1 hour. After solution was thrown away, washed by PBS-Tween three times (200 μL/well). PBS-Tween solution of 3D11-HPR (1 μg/mL, 50 μL/well) was added and left for one hour at room temperature. The solution was thrown away and washed by PBS-Tween three times (200 μL/well), then OPD solution (100 μL/well, Sigma Co., Ltd. FAST (™ o-PHNYLENE DIAMINE DIHYDROCHLORIDE SETS is used) was added and processed for color reaction for 5-10 minutes at room temperature. 2N sulfuric acid aqueous solution (50 μL/well) was added so as for the reaction to be stopped and absorbance (450 nm) was measured by Microplate Reader Benchmark of Bio-Rad Co., Ltd. Measuring results were summarized in FIG. 3.

POSSIBILITY FOR THE INDUSTRIAL USE

As mentioned above, the inventors of the present invention have found that ciguatoxins can be detected with a high sensitivity by utilizing Sandwich ELISA method using combination of two kinds of monoclonal antibodies which are obtained by using the synthetic hapten having IJKLM ring fragment of ciguatoxins and the synthetic hapten having ABCDE ring fragment of ciguatoxins respectively. In the conventional toxin detective kits which use only one antibody having a patial fragment of ciguatoxins capable of binding to the samples, it is impossible to avoid the result of false positive caused by the antibody bonding with contamination. In the conventional technique, it is impossible to distinguish whether it is false positive or not, the immunoassay kits of the present invention contributes to improve the safety of social life remarkably. The sandwich immunoassay kit using the combination of two kinds of antibodies to detect non-protein molecule is established by the present invention for the first time, and especially, provides excellent effect from the view point of the establishment of the detective method with height specificity to ciguatoxin CTX3C.

Illustration of the Abbreviations

BSA: bovine serum albumin

CTX: ciguatoxin

ELISA: enzyme linked immunosorbent assay

HRP: Horseradish Peroxidase

O.D.: Optical Density

OPD: o-Phenylene Diamine

PBS: Phosphate Buffered Saline

Bn: benzyl

DDQ: 2,3-dichloro-5,6-dicyano-1,4-benzoquinone

EDC: 1-(3-dimethylaminopropyl)-3-ethylcarbodiimide hydrochloride

FCS: fetal calf serum

Ig: Immunoglobulin

KLH: keyhole limpet hemocyanine

TBAF: tetra-n-butylammonium fluoride

Ts: p-tolenesulfonyl

THF: tetrahydrofuran

OVA: ovalbumin

The invention claimed is:

1. A sandwich immunoassay kit, comprising of two monoclonal antibodies that are prepared by using synthetic haptens represented by formula 1 and formula 2, and are produced from hybridoma 3D11 deposited under accession number FERM PB-8293 and 10C9 deposited under accession number FERM PB-8292, respectively, formula 1

[formula 1 structure]

[formula 2 structure]

wherein, R is H or methyl group.

2. The sandwich immunoassay kit of claim 1, wherein one of the monoclonal antibodies is labeled.

3. The sandwich immunoassay kit of claim 2, wherein one of the monoclonal antibodies is labeled with an enzyme.

4. A compound represented by formula 1 formula 1

[formula 1 structures]

where R is H or methyl group.

5. Hybridoma 3D11 that produces the monoclonal antibody against ciguatoxins, which is deposited at International Patent Organism Depository (IPOD) of Advanced Industrial Science and Technology (AIST) in Japan under accession number FERM PB-8293.

6. Hybridoma 10C9 deposited at International Patent Organism Depository (IPOD) of Advanced Industrial Science and Technology (AIST) in Japan under accession number FERM PB-8292 that produces a monoclonal antibody against ciguatoxin CTX3C.

* * * * *